US00PP27667P3

(12) United States Plant Patent
Fretwell

(10) Patent No.: US PP27,667 P3
(45) Date of Patent: Feb. 14, 2017

(54) ***CLEMATIS* PLANT NAMED 'BFCCRAP'**

(50) Latin Name: *Clematis texensis*
Varietal Denomination: BFCCRAP

(71) Applicant: Barry Fretwell, Exeter (GB)

(72) Inventor: Barry Fretwell, Exeter (GB)

( * ) Notice: Subject to any disclaimer, the term of this patent is extended or adjusted under 35 U.S.C. 154(b) by 60 days.

(21) Appl. No.: 14/545,412

(22) Filed: Apr. 30, 2015

(65) Prior Publication Data

US 2016/0324052 P1 Nov. 3, 2016

(51) Int. Cl.
*A01H 5/02* (2006.01)

(52) U.S. Cl.
USPC ..... Plt./228

(58) Field of Classification Search
USPC ..... Plt./228
See application file for complete search history.

*Primary Examiner* — Keith Robinson
(74) *Attorney, Agent, or Firm* — Cassandra Bright

(57) ABSTRACT

A new and distinct *Clematis* hybrid named 'BFCCRAP' is disclosed, characterized by a distinctive bright pink flowers with unusual long, undulating tepals. Plants have a dense, shrubby plant form and are well suited for container plantings. Flowers are produced from June through September. The new cultivar is a *Clematis* typically suited for ornamental container and landscape use.

1 Drawing Sheet

Latin name of the genus and species: *Clematis texensis*.
Variety denomination: 'BFCCRAP'.

BACKGROUND OF THE INVENTION

The new cultivar is the result of planned breeding program, conductor by the inventor, Barry Fretwell in Exeter, Great Britain. The seed parent is an unnamed, unpatented, proprietary *Clematis texensis*, the pollen parent is also an unnamed, unpatented, proprietary *Clematis texensis*. The cross was made during 2005 and the selection of the new variety was made in 2007.

After selecting and isolating the new cultivar, asexual reproduction of the new cultivar 'BFCCRAP' was first performed in Exeter, Great Britain at a nursery by vegetative cuttings in 2008. 'BFCCRAP' has since produced multiple generations, and has shown that the unique features of this cultivar are stable and reproduced true to type.

The inventor has applied for Plant Breeder's Rights protection in Europe during December 2013. The CPVO File Number is 2013/3222. However, plants were not available to the public until May 20, 2104 by an offer for sale through F. M. Westphal, a company in Germany. The inventor confirms, the company Westphal received plant material directly from the inventor. As this first public sale originated from a source receiving material directly from the inventor, and occurred within one year of this filing, the inventor believes he has met the requirement of U.S.C. 102(b). A copy of the EU application is included with this application at the time of deposit. The EU application verifies that at the time of filing in the EU, no sales had occurred.

SUMMARY OF THE INVENTION

The cultivar 'BFCCRAP' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BFCCRAP'. These characteristics in combination distinguish 'BFCCRAP' as a new and distinct *Clematis* cultivar:

1. Unusual long, undulating tepals.
2. Bright pink flowers.
3. Flowering from June through September.
4. Dense plant habit.
5. Suitability for container culture.

PARENTAL COMPARISON

Plants of the new cultivar 'BFCCRAP' are similar to the seed parent variety in most horticultural characteristics. However, the new variety differs from the seed parent in the following:

1. Different colored flowers.
2. Different flower type.

Plants of the new cultivar differ from the pollen parent in the following:

1. Different colored flowers.
2. Different flower type.
3. Shorter internode length.

COMMERCIAL COMPARISON

Plants of the new cultivar 'BFCCRAP' are similar to the commercial variety *Clematis texensis* 'Duchess of Albany', unpatented, in most horticultural characteristics. However, the new variety differs from 'Duchess of Albany' in the following:

1. The new variety has longer, more undulating tepals.
2. The new variety has brighter pink flowers.
3. Plants of the new variety are more compact.

The new variety can also be compared to *Clematis texensis* 'Princess Diana', unpatented, differing in the following characteristics:

1. The new variety has larger flowers.
2. The new variety has flowers with a semi-open shape, whereas this comparator has tubular, tulip like flowers.
3. The new variety has a shorter internode length.
4. The new variety has a slightly darker flower color.
5. the new variety has different shaped foliage.

BRIEF DESCRIPTION OF THE PHOTOGRAPH

The accompanying photograph in FIG. 1 illustrates in full color a typical mature flowers and foliage of 'BFCCRAP' grown outdoors in Germany. Age of the plant is approximately 8 months. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'BFCCRAP' plants grown outdoors in Germany. The growing temperature ranged from 0° C. to 25° C. at night to 0° C. to 30° C. during the day. No artificial light, photoperiodic treatments or chemical treatments were given to the plants. Plants were pinched twice. Measurements and numerical values represent averages of typical flowering types.

Botanical classification: *Clematis texensis* 'BFCCRAP'.

Age of the plant described: Approximately 8 months.

Container size of the plant described: Growing in the ground.

PROPAGATION

Typical method: Vegetative cuttings.

Time to initiate root developments: 24 days in the summer at 22° to 26° C.

Time to produce a rooted cutting/young plant: 50-60 days in the summer at 20° to 26° C.

Root description: Fine, fibrous.

PLANT

Growth habit: Shrubby, semi-climbing vine.

Time to produce a finished flowering plant: Approximately 12-14 months from an un-rooted cutting to a deliverable plant, in a 1.5 or 2 Liter size container.

Height: Approximately 8 to 10 feet, measured from the soil line of the ground after approximately 8 months.

Plant spread: Approximately 2 to 3 feet.

Growth rate: Rapid during active growing season in Spring. 30 to 40 cm per month.

Branching characteristics: One main stem, easily making side branches from a pinch. Typically 2 to 4 main lateral branches form from a pinch.

Length of main stem: Approximately 200 to 300 cm.

Diameter of main stem: Approximately 0.3 cm.

Main stem color: Near RHS Green 143C, flushed with Greyed-Purple 183B.

Main stem texture: Glabrous.

Internode length: Varies from 5 to 12 cm.

Strength: Strong, flexible, semi-woody.

FOLIAGE

Leaf:

*Arrangement*.—Opposite, simple.

*Leaves per lateral branch*.—Average range 3 to 7.

*Average length*.—Approximately 6 to 10 cm.

*Average width*.—Approximately 4 to 5 cm.

*Shape of blade*.—Cordate.

*Apex*.—Acute.

*Base*.—Cordate.

*Attachment*.—Stalked.

*Margin*.—Entire.

*Texture upper and lower surfaces*.—Glabrous.

*Color*.—Young foliage upper side: Near RHS Green 137A. Young foliage under side: Near RHS Green 137A. Mature foliage upper side: Near RHS Green 137A. Mature foliage under side: Near RHS Green 137A.

*Venation*.—Type: Pinnate. Venation color upper side: Near RHS Green 137C. Venation color under side: Near RHS Green 138A.

Petiole:

*Length*.—Approximately 6.0 to 8.0 cm.

*Diameter*.—Approximately 0.2 cm.

*Texture*.—Smooth.

*Color*.—Near RHS Green 143C, flushed with Greyed-Purple 183B.

FLOWER

Bloom period:

*Natural season*.—June through September.

Inflorescence type and habit: Axillary, solitary, rotate. Flowers facing outward and slightly upward. Flowering occurring on both previous year's growth and current year's growth.

Quantity of flowers and buds on the plant at a given time: 50 to 70.

Rate of flower opening: Approximately 10 days from bud to fully opened flower.

Flower longevity on plant: Approximately 10 to 14 days, after fully opened. Self-cleaning.

Inflorescence size:

*Diameter*.—Approximately 12.0 cm.

*Depth*.—Approximately 7.0 cm.

Flowers:

*Corolla*.—Tepal arrangement: slightly overlapping single whorl, upwardly cupped. Quantity: Typically 4 to 6 per flower. Size: Length: Approximately 7.0 cm. Width: Approximately 2.0 cm. Margin: Undulating, entire. Apex: Acuminate. Base: Blunt. Texture: Smooth.

*Color*.—Tepals: When opening: Upper surface: Near RHS Red-Purple N57A. Lower surface: Near RHS Red-Purple N57B. Fully opened: Upper surface: Near RHS Red-Purple N57B, N57C and very faint streaks near 62D. Lower surface: Near RHS Red-Purple N57C and very faint streaks near 62D. Ageing: Upper surface: Near RHS Red-Purple N57D and very faint streaks near 62D. Lower surface: Near RHS Red-Purple 62B and very faint streaks near 62D.

*Bud*.—Shape: Conical. Length: Approximately 3.5 cm. Diameter: Approximately 2.0 cm. Color: Near RHS Red-Purple 58D.

*Peduncles*.—Length: Average 10 cm. Width: Approximately 0.3 cm. Angle: Average 90°. Strength: Flexible. Color: Near RHS Greyed-Purple 183B.

*Fragrance*.—None.

REPRODUCTIVE ORGANS

Stamens:

*Number*.—Average 40 to 50 per flower.

*Stamen color*.—Near Red-Purple 62D.

*Stamen length*.—Average 2.8 cm.

*Anther length*.—Approximately 0.08 to 0.12 cm.

*Anther color*.—Near RHS Red-Purple 62D.

*Anther shape*.—Oblong.

*Pollen quantity*.—Moderate.

*Pollen color*.—Near White N155C.

Pistil:

*Pistil quantity*.—40 to 50 per flower.

*Length*.—Approximately 0.8 cm.

*Style length*.—Approximately 0.6 cm.

*Style color*.—Near RHS White N155C.

*Stigma*.—Shape: Linear. Color: Near RHS White N155C.

OTHER CHARACTERISTICS

Seeds and fruits: Not observed to date.

Disease/pest resistance: Neither resistance nor susceptibility to normal diseases and pests of *Clematis* has been observed.

Temperature tolerance: Tolerates temperatures from approximately −25° C. to 45° C.

What is claimed is:

1. A new and distinct cultivar of *Clematis* hybrid plant named 'BFCCRAP' as herein illustrated and described.

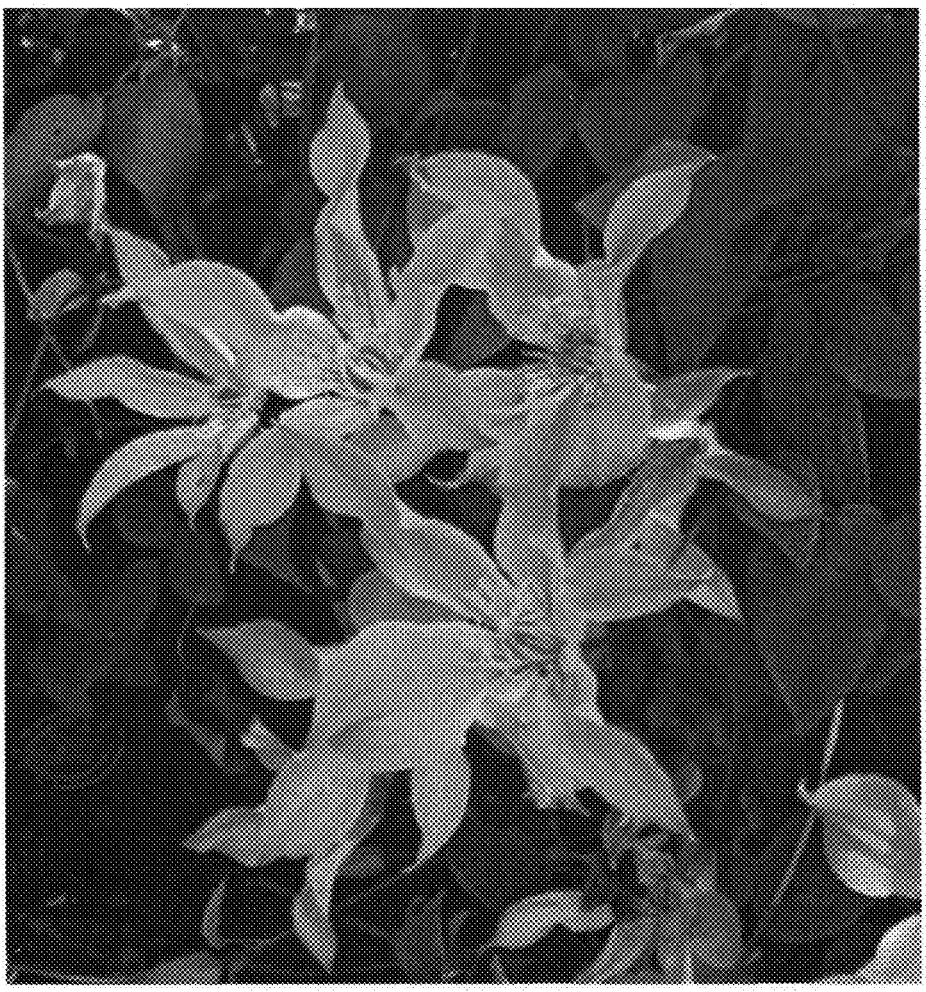

* * * * *